United States Patent [19]
Buonomo

[11] Patent Number: 5,962,416
[45] Date of Patent: Oct. 5, 1999

[54] ACCELERATING ANIMAL HOOF GROWTH WITH SOMATOTROPIN

[75] Inventor: Frances Catherine Buonomo, Wildwood, Mo.

[73] Assignee: Monsanto Company, St. Louis, Mich.

[21] Appl. No.: 09/105,651

[22] Filed: Jun. 26, 1998

Related U.S. Application Data

[60] Provisional application No. 60/051,111, Jun. 27, 1997.

[51] Int. Cl.$^6$ .......................... A61K 38/25; A61K 38/27
[52] U.S. Cl. .............................................. 514/12; 514/21
[58] Field of Search ..................... 530/324, 399; 514/12, 21; 930/120

[56] References Cited

U.S. PATENT DOCUMENTS

| | | | |
|---|---|---|---|
| 3,915,170 | 10/1975 | Nyssen ..................................... | 606/212 |
| 4,604,283 | 8/1986 | Gresham ................................... | 424/80 |
| 4,863,736 | 9/1989 | Azain et al. ............................. | 424/423 |
| 5,086,041 | 2/1992 | Mitchell .................................... | 514/12 |
| 5,130,422 | 7/1992 | Krivi et al. ............................... | 536/27 |
| 5,232,708 | 8/1993 | Castillo et al. ........................... | 424/497 |
| 5,454,832 | 10/1995 | Favicchia ................................ | 606/212 |
| 5,595,752 | 1/1997 | Kasser et al. ............................ | 424/423 |
| 5,616,332 | 4/1997 | Herstein ................................... | 424/401 |

FOREIGN PATENT DOCUMENTS

| | | | |
|---|---|---|---|
| 0 192 629 A2 | 8/1986 | European Pat. Off. .......... | C07K 3/00 |
| 0 274 369 B1 | 9/1990 | European Pat. Off. ....... | A01N 57/20 |

OTHER PUBLICATIONS

Buonomo et al. The Effects of Bovine Somatotropin . . . J. Anim.Sci. vol. 74, No. 4, pp. 886–894, Apr. 1996.

Abdel–Meguid, Sherin S. et al. (1987) "Three-dimensional structure of a genetically engineered variant of porcine growth hormone," *Proc. Natl. Acad. Sci. USA* 84:6434–6437.

Argente, J. et al. (1996) "Growth hormone-releasing peptides: clinical and basic aspects," *Horm Res* 46(4–5):155–159 (Abstract only attached0.

Buonomo, F. C. et al. (1996) "The Effects of Bovine Somatotropin (bST) and Porcine Somatotropin (pST) on Growth Factor and Metabolic Variables in Horses," *J. Anim. Sci.* 74:886–894.

(List continued on next page.)

*Primary Examiner*—Jeffrey E. Russel
*Attorney, Agent, or Firm*—George R. Beck; Arnold, White & Durkee

[57] ABSTRACT

Animal hoof growth is accelerated by the administration of a compound having somatotropin-like activity or a compound which causes the secretion of somatotropin in the animal. The method is applicable to any situation in which increased hoof growth is desired. A particularly important application of this method relates to the treatment of cracked hooves, wherein an animal having a cracked hoof is treated with somatotropin in order to reduce the recovery time from the injury.

10 Claims, 1 Drawing Sheet

OTHER PUBLICATIONS

Early, R. J. et al. (1990) Growth and Metabolism in Somatotropin–Treated Steers: II. Carcass and Noncarcass Tissue Components and Chemical Compositions, *J. Anim. Sci.* 68:4144–4152.

Enright, W. J. et al. (1989) "Effects of infusions of various doses of bovine growth hormone–releasing factor on blood hormones and metabolites in lactating Holstein cows." *J. Endocrinol.* 122(3):671–679 (Abstract only attached.).

International Search Report PCT/US 98/13117, dated Jan. 25, 1999.

Nichels, F. A. (1997) "Hoof Cracks," In: *Current Therapy in Equine Medicine*, vol. 2, Robinson, N.E. (ed.), W. B. Saunders, Phil, PA (pub.).

Roberge, S. et al. (1992) "Evaluation of the biological potency of new agmatine analogs of growth hormone–releasing hormone in the bovine," *Proc. Soc. Exp. Biol. Med.* 200(1):109–114 (Abstract only attached.).

Scarborough, R. et al. (1988) "Analogs of growth hormone–releasing hormone induce release of growth hormone in the bovine," *J. Anim. Sci.* 66(6):1386–1392 (Abstract only attached).

Seeburg, Peter H. et al. (1983) "Eficient Bacterial Expression of Bovine and Porcine Growth Hormones," *DNA* 2(1):37–45.

Thomas, G.B. et al. (1997) "Activation of the hypothalamo–pituitary–adrenal axis by the growth Hormone (GH) secretagogue, GH–releasing peptide–6, in rats," *Endocrinology* 138(4):1585–1591 (Abstract only attached.)

Zarandi, M. et al. (1992) "Potent agonists of growth hormone–releasing hormone. Part I.," Int. *J. Pept. Protein Res.* 39(3):211–217 (Abstract only attached).

ical impact/trauma, poor hoof and leg

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 216 amino acids
      (B) TYPE: amino acid
      (C) STRANDEDNESS:
      (D) TOPOLOGY: linear (xi) SEQUENCE DESCRIPTION: SEQ ID NO:1:

```
Met Ala Ala Gly Pro Arg Thr Ser Val Leu Leu Ala Phe Gly Leu Leu
1               5                   10                  15

Cys Leu Pro Trp Pro Gln Asp Val Gly Ala Phe Pro Ala Met Pro Leu
            20                  25                  30

Ser Ser Leu Phe Ala Asn Ala Val Leu Arg Ala Gln His Leu His Gln
        35                  40                  45

Leu Ala Ala Asp Thr Tyr Lys Glu Phe Glu Arg Ala Tyr Ile Pro Glu
    50                  55                  60

Gly Gln Arg Tyr Ser Ile Gln Asn Ala Gln Ala Phe Cys Phe Ser
65                  70                  75                  80

Glu Thr Ile Pro Ala Pro Thr Gly Lys Asp Glu Ala Gln Gln Arg Ser
                85                  90                  95

Asp Met Glu Leu Leu Arg Phe Ser Leu Leu Ile Gln Ser Trp Leu
            100                 105                 110

Gly Pro Val Gln Leu Leu Ser Arg Val Phe Thr Asn Ser Leu Val Phe
            115                 120                 125

Gly Thr Ser Asp Arg Val Tyr Glu Lys Leu Arg Asp Leu Glu Glu Gly
130                 135                 140

Ile Gln Ala Leu Met Arg Glu Leu Glu Asp Gly Ser Pro Arg Ala Gly
145                 150                 155                 160

Gln Ile Leu Lys Gln Thr Tyr Asp Lys Phe Asp Thr Asn Leu Arg Ser
                165                 170                 175

Asp Asp Ala Leu Leu Lys Asn Tyr Gly Leu Leu Ser Cys Phe Lys Lys
            180                 185                 190

Asp Leu His Lys Ala Glu Thr Tyr Leu Arg Val Met Lys Cys Arg Arg
            195                 200                 205

Phe Val Glu Ser Ser Cys Ala Phe
    210                 215

(2) INFORMATION FOR SEQ ID NO:2:

(i) SEQUENCE CHARACTERISTICS:
        (A) LENGTH: 217 amino acids
        (B) TYPE: amino acid
        (C) STRANDEDNESS:
        (D) TOPOLOGY: linear (xi) SEQUENCE DESCRIPTION: SEQ ID NO:2:

Met Met Ala Ala Gly Pro Arg Thr Ser Leu Leu Leu Ala Phe Ala Leu
1               5                   10                  15

Leu Cys Leu Pro Trp Thr Gln Val Val Gly Ala Phe Pro Ala Met Ser
            20                  25                  30

Leu Ser Gly Leu Phe Ala Asn Ala Val Leu Arg Ala Gln His Leu His
        35                  40                  45

Gln Leu Ala Ala Asp Thr Phe Lys Glu Phe Glu Arg Thr Tyr Ile Pro
    50                  55                  60

Glu Gly Gln Arg Tyr Ser Ile Gln Asn Thr Gln Val Ala Phe Cys Phe
65                  70                  75                  80

Ser Glu Thr Ile Pro Ala Pro Thr Gly Lys Asn Glu Ala Gln Gln Lys
                85                  90                  95

Ser Asp Leu Glu Leu Leu Arg Ile Ser Leu Leu Leu Ile Gln Ser Trp
            100                 105                 110

Leu Gly Pro Leu Gln Phe Leu Ser Arg Val Phe Thr Asn Ser Leu Val
            115                 120                 125

Phe Gly Thr Ser Asp Arg Val Tyr Glu Lys Leu Lys Asp Leu Glu Glu
130                 135                 140
```

```
Gly Ile Leu Ala Leu Met Arg Glu Leu Glu Asp Gly Thr Pro Arg Ala
145                 150                 155                 160

Gly Gln Ile Leu Lys Gln Thr Tyr Asp Lys Phe Asp Thr Asn Met Arg
            165                 170                 175

Ser Asp Asp Ala Leu Leu Lys Asn Tyr Gly Leu Leu Ser Cys Phe Arg
                180                 185                 190

Lys Asp Leu His Lys Thr Glu Thr Tyr Leu Arg Val Met Lys Cys Arg
            195                 200                 205

Arg Phe Gly Glu Ala Ser Cys Ala Phe
    210                 215
```

(2) INFORMATION FOR SEQ ID NO:3:

(i) SEQUENCE CHARACTERISTICS:
       (A) LENGTH: 216 amino acids
       (B) TYPE: amino acid
       (C) STRANDEDNESS:
       (D) TOPOLOGY: linear (xi) SEQUENCE DESCRIPTION: SEQ ID NO:3:

```
Met Ala Ala Gly Pro Arg Thr Ser Ala Leu Leu Ala Phe Ala Leu Leu
1               5                   10                  15

Cys Leu Pro Trp Thr Arg Glu Val Gly Ala Phe Pro Ala Met Pro Leu
            20                  25                  30

Ser Ser Leu Phe Ala Asn Ala Val Leu Arg Ala Gln His Leu His Gln
            35                  40                  45

Leu Ala Ala Asp Thr Tyr Lys Glu Phe Glu Arg Ala Tyr Ile Pro Glu
    50                  55                  60

Gly Gln Arg Tyr Ser Ile Gln Asn Ala Gln Ala Ala Phe Cys Phe Ser
65                  70                  75                  80

Glu Thr Ile Pro Ala Pro Thr Gly Lys Asp Glu Ala Gln Gln Arg Ser
                85                  90                  95

Asp Val Glu Leu Leu Arg Phe Ser Leu Leu Leu Ile Gln Ser Trp Leu
                100                 105                 110

Gly Pro Val Gln Phe Leu Ser Arg Val Phe Thr Asn Ser Leu Val Phe
            115                 120                 125

Gly Thr Ser Asp Arg Val Tyr Glu Lys Leu Lys Asp Leu Glu Glu Gly
130                 135                 140

Ile Gln Ala Leu Met Arg Glu Leu Glu Asp Gly Ser Pro Arg Ala Gly
145                 150                 155                 160

Gln Ile Leu Lys Gln Thr Tyr Asp Lys Phe Asp Thr Asn Leu Arg Ser
            165                 170                 175

Asp Asp Ala Leu Leu Lys Asn Tyr Gly Leu Leu Ser Cys Phe Lys Lys
                180                 185                 190

Asp Leu His Lys Ala Glu Thr Tyr Leu Arg Val Met Lys Cys Arg Arg
            195                 200                 205

Phe Val Glu Ser Ser Cys Ala Phe
    210                 215
```

ACCELERATING ANIMAL HOOF GROWTH WITH SOMATOTROPIN This application is based on U.S. Provisional Application No. 60/051,111, filed Jun. 27, 1997.

BACKGROUND OF THE INVENTION

Horses and other hoofed animals are susceptible to numerous injuries and ailments associated with defects in their hooves. Cracked hooves, for example, are a common occurrence in horses and can render an animal unserviceable for extended periods of time, typically 6 months to a year for medium or large sized cracks, until the entire hoof has had sufficient time to regrow.

The horse hoof is a non-vascular cornified epidermis of the animal's foot consisting of a wall, a sole and a frog. The wall is made from keratinized epithelial cells which overlay a sensitive lamellar corium tissue containing water in addition to numerous minerals. The ground surface of the hoof can be divided into three zones: the toe zone, the quarter zone, and the heel zone, all of which are susceptible to cracking.

Horse hoof cracks can be caused by essentially anything that impairs the elasticity of the hoof, weakens it, or causes overloading. The most frequent causes of hoof cracks include physical impact/trauma, poor hoof and leg conformation, imbalance of the hoof, improper trimming or shoeing, and invasion of the white-line by bacteria, fungus or mold. Genetic predisposition, nutritional imbalances, dry or brittle hooves, or those having excessively thin walls, can represent predisposing factors to hoof cracking. Once a crack occurs, the hoof wall often pinches and irritates the underlying laminae within the hoof capsule due to the expansion and contraction of the hoof during loading and unloading. Lameness and/or extended unserviceability is an unfortunate and costly consequence of many cracked hooves.

Various approaches have been used to minimize the difficulties associated with hoof cracks. Typically, treatment involves an attempt to remove pressure from the free extremity of the crack and immobilize its edges. Conventional methods for repair include proper balancing of the hoof, corrective shoeing, grooving of the hoof wall, use of clamping across the crack with nails, a Vachette clamp, or mechanical clamps, and use of various prosthetic hoof repair materials such as acrylic, fiberglass, or epoxy resins in combination with umbilical tape or wire, sheet metal screws, or other synthetic materials. (See for example, Nickels, F. A., "Hoof Cracks", In: Current Therapy in Equine Medicine, vol. 2, Robinson, N. E. (ed.), W. B. Saunders, Phil, Pa. (pub.), 1997)

Lacking from the prior art, however, are effective biologically-based approaches for treating hoof injuries. Methods for accelerating the rate of hoof growth would be desirable because they could significantly reduce the length of time required for an animal to recover from a cracked or otherwise injured hoof.

Somatotropins, also known as growth hormones, are polypeptides produced and secreted by cells of the pituitary gland. These proteins, which can be produced reliably and inexpensively in large quantities by recombinant DNA technology, are known to be effective in promoting pre-adult skeletal growth and meat production of beef cattle and swine. In addition, they are known to affect a variety of metabolic processes including the stimulation of lactation, improvements of the efficiency of converting feed to meat or milk, and lipid-mobilizing effects.

SUMMARY OF THE INVENTION

The present invention provides in it's broadest sense a biologically-based approach to manipulating hoof growth in hoof-bearing animals. Thus, any application in which it would be desirable to accelerate hoof growth could use the method of the present invention to achieve such a result.

In accordance with a first aspect of the present invention, there is provided a method of accelerating hoof growth in a hoofed animal. The method involves the administration, typically parenterally, of a compound having somatotropin-like activity or a compound which causes the secretion of somatotropin in the animal. Preferred compounds suitable for use in accordance with the methods disclosed herein are equine, bovine, or porcine somatotropins, or variants derived therefrom having at least 80% homology to the naturally occurring equine somatotropin protein.

In accordance with a second aspect of the present invention, there is provided a method of treating a cracked horse hoof wherein a compound having somatotropin-like activity or a compound which causes the secretion of somatotropin in the horse is administered in an amount effective for accelerating hoof growth. The method can be used as the sole form of treatment, or may be used in combination with conventional hoof crack repair techniques. The use of such compounds in the treatment of cracked hooves can significantly reduce the time that it takes an animal to recover from such an injury by reducing the time typically required for hoof regrowth.

BRIEF DESCRIPTION OF THE DRAWING

The following drawing forms part of the present specification and is included to further demonstrate certain aspects of the present invention. The invention may be better understood by reference to the drawing in combination with the detailed description of specific embodiments presented herein.

DESCRIPTION OF ILLUSTRATIVE EMBODIMENTS

Figure 1:
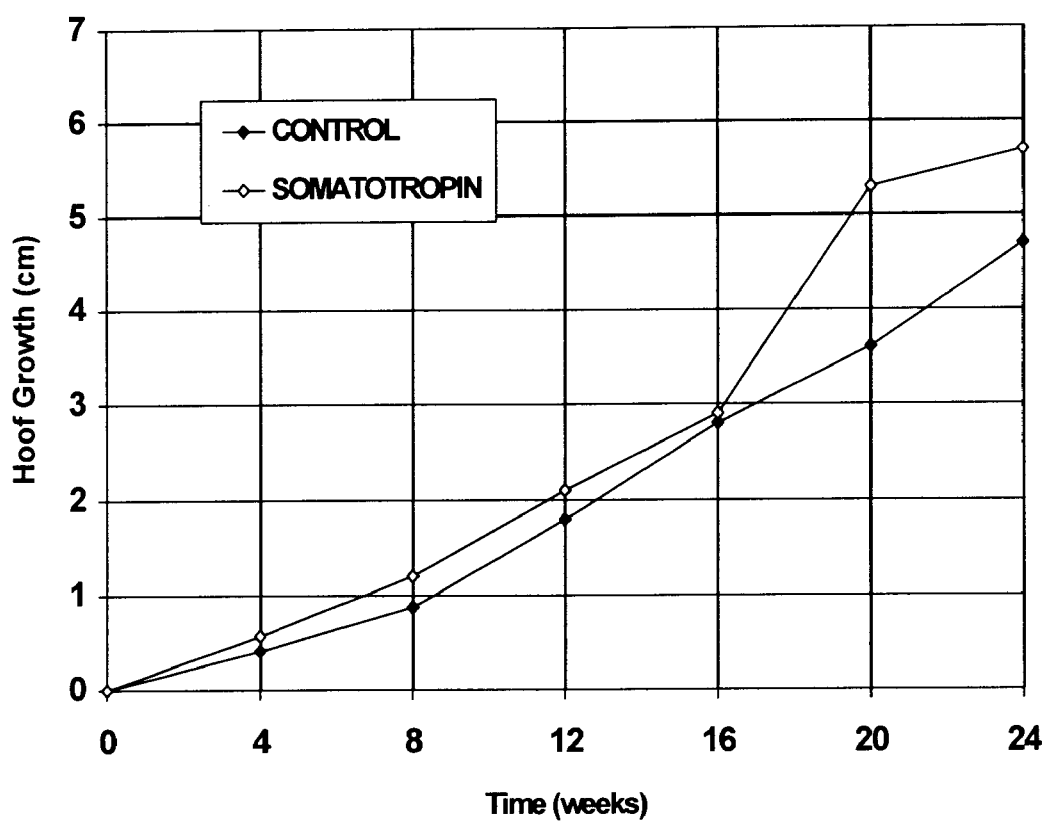
FIG. 1 compares hoof growth over a 24 week period for horses treated with 10 mg/animal/day somatotropin (n=6) and control horses receiving only excipient (n=6). Over the 24 week study, hoof length in the somatotropin-treated group increased by 26.2% (p<0.0001).

As used herein, the following terms have the meanings set forth below:

"Somatotropin" refers to any polypeptide that has biological activity and chemical structure similar to that of a somatotropin produced in the pituitary gland of an animal. Such somatotropins include natural somatotropins produced by the pituitary somatotropic cells and, alternatively, somatotropin produced by recombinant DNA technology in which a somatotropin, or a variant derived therefrom, is expressed by genetically transformed prokaryotic or eukaryotic cells, e.g. bacteria (such as *E. coli*), yeast or algae.

"Compound having somatotropin-like activity" refers to a compound that is related structurally and/or functionally to a mammalian somatotropin. For the purposes of this disclosure, such a compound is at least 80% homology to the naturally occurring equine somatotropin protein and/or exhibits biological activity of the kind associated with naturally occurring somatotropins, i.e., binds to a somatotropin receptor with sufficient affinity to result in improvement of growth, lactation, feeding efficiency and/or health of the animal.

"Compound which causes the secretion of somatotropin" refers to any compound e.g., growth hormone releasing factors/peptides/mimetics, that causes in the animal being treated an increase in the production and/or secretion of endogenous somatotropin.

"Parenteral" administration refers to the administration of a bioactive material directly to an animal by injection or implantation as opposed to topical or oral administration. Parenteral administration by implantation of solid compositions may be intramuscular, subcutaneous or intraperitoneal, and may be accomplished by injecting a solid, suspension or solution of the somatotropin using a syringe, injection gun or other instrument designed for that purpose.

It has now been found that somatotropins can accelerate hoof growth when administered to hoof-bearing animals. This discovery has particularly important applications in the treatment of hoof injuries, especially cracked hooves. Furthermore, the method has applicability to any situation in which rapid hoof growth in an animal would be desired.

In a first embodiment of the present invention, there is provided a method of accelerating hoof growth in a hoofed animal. The method involves treatment of the animal with an effective amount of a compound having somatotropin-like activity or a compound which causes secretion of somatotropin so as to increase the growth rate of the animal's hooves.

Any protein or compound having somatotropin-like activity is suitable for practice of the present invention. These may include polypeptides having identical amino acid sequences to the naturally occurring somatotropins or may be endogenous or experimentally generated variants of the natural sequences which have substantially the same or enhanced activity compared to naturally occurring somatotropin proteins. Such variants may include, for example, amino acids either added to, subtracted from, or substituted for the amino acid sequence of the naturally occurring material. Numerous somatotropin variants are known in the art which would be suitable for use in accordance with the present invention. For example, many somatotropins produced using recombinant DNA retain an extraneous methionine moiety at their amino terminus. Other somatotropin variants have the asparagine residue located in the 95–101 amino acids region replaced by glutamine, as described in U.S. Pat. No. 5,130,422.

Also suitable for use in the present invention are compounds which can cause the secretion of somatotropin in animals. Many such compounds are well known in the art and include, for example, naturally occurring mammalian growth hormone releasing hormones (GHRH) or analogs thereof (see for example, J. Anim. Sci. 66 (6) 1386–92, 1988) or agonists of GHRH (see for example, Int. J. Pept. Prot. Res. 39(3) 211–17, 1992). Synthetic growth hormone releasing peptides (GHRP) (see for example, Horm. Res. 46 (4-5) 155–9, 1996) are also suitable for use in the present invention. One skilled in the art would recognize that the numerous approaches which have been developed for stimulating endogenous somatotropin secretion are within the scope of this invention.

Any mammalian somatotropin is suitable for the practice of this invention based upon the substantial homology and cross-species activity of somatotropins in certain animals. For example, Buonomo et al. (J. Anim. Sci. 74: 886–894, 1996) reported that porcine somatotropin (pST) and bovine somatotropin (bST) are biologically active in the equine species, and can elicit metabolic responses to exogenously administered somatotropin in a manner similar to the responses observed in other mammalian species. For examples of known somatotropin amino acid sequences see European Patent Application No. 192,629 filed Aug. 27, 1986, Seeberg et al., DNA Vol. 2, No. 1, p. 37–45, 1983, and Abdel-Meguid et al., Proc. Natl. Acad. Sci., USA, vol.84, pp. 6434–6437, September 1987. The amino acid sequences of equine somatotropin (eST), bovine somatotropin and porcine somatotropin are shown in SEQ ID NOs. 1, 2 and 3 respectively. eST is 98.4% homologous to pST and 89.5% homologous to bST.

Also suitable for use in the present invention are somatotropins which are associated with anions or cations, particularly salts, complexes or other combinations with metal ions. Examples of suitable monovalent metal ions include sodium and potassium while examples of suitable polyvalent metal ions include zinc, iron, calcium, bismuth, barium, magnesium, manganese, aluminum, copper, cobalt, nickel and cadmium. Suitable anions may include bicarbonate, acetate, glycine, and borate. Bovine and porcine somatotropins prepared by recombinant DNA technology and metal complexes thereof are described, for example, in U.S. Pat. No. 4,863,736.

The somatotropins of this invention could be prepared by chemical synthesis. However, owing to the large size of the somatotropin molecule, it is preferred to prepare them by recombinant DNA technology. This can be done by conventional means by constructing a gene encoding the desired somatotropin or variant thereof. A convenient method of constructing a variant somatotropin gene is by conventional oligonucleotide-directed site-specific mutagenesis of the natural gene. The mutated gene is then cloned into an appropriate vector and subsequently used to transform a suitable expression host, such as bacteria (e.g. *E. coli* or Psuedomonas), yeast (e.g. *S.cerviseae*), or mammalian cells (e.g. C127 or CHO). The somatotropin is then expressed, folded into its biologically active configuration, purified and recovered using any suitable, e.g., conventional, methodologies.

Efficacy will vary depending upon the size and maturity of the animal, the amount of somatotropin administered, and the type of delivery system employed. Generally, the greater the amount of somatotropin given to an animal, the greater the resulting acceleration of hoof growth. Typically, the animal is administered somatotropin in an amount greater than 1 ug/kg/day. The upper dosage limit can be between about 50 to 250 ug/kg/day and will depend upon the size of the horse. This upper limit is dictated by the known diabetogenic effects of prolonged administration of high doses of somatotropin. Preferably, the dose administered is between about 10 to 100 ug/kg/day for an average sized horse (e.g. 300–600 kg). Such doses can be maintained for extended periods of time (e.g. 4–6 months or more) without adversely compromising the health of the animal.

Other materials may be present in the somatotropin composition administered to an animal provided such materials do not unacceptably inhibit desired efficacy. For example, vehicles such as saline, an oil (preferably vegetable), a glycerol or tocopherol-like compound, an anti-inflammatory, or other additive, may be present to prevent or counteract the effects of foreign body (e.g. non-allergic) reaction. Such additives can include steroid and/or non-steroid anti-inflammatory agents which preferably are present in the composition at a level low enough to avoid any systemic effect but sufficient to be effective in reducing local inflammation.

Pelletized somatotropin compositions may be made by dry compression using standard tabletting techniques. If desired, binders, lubricants, fillers and the like may be present in the compositions to facilitate the tabletting process while bacteriostats, antioxidants, anti-inflammatory agents, antibiotics and the like may be present for their therapeutic effects. Suitable solid pellets of somatotropin adapted for parenteral administration by implantation are described, for example, in U.S. Pat. No. 4,863,736.

The somatotropin compositions may be administered by known techniques effective for delivery of desired doses to an animal being treated. These include, for example, intramuscular, intraperitoneally or subcutaneous injections, or by the use of any controlled release implant, or other prolonged release compositions known in the art. For example, prolonged release somatotropin compositions could comprise somatotropin polypeptide in the presence of a biocompatible oil as disclosed in U.S. Pat. No. 5,086,041. Alternatively, the somatotropin could be administered in the form of a pellet implant coated with polyvinyl alcohol, as disclosed in U.S. Pat. No. 5,232,708. Numerous other methods of administering bioactive molecules are known in the art and are applicable to the administration of somatotropin in accordance with the present invention for the purpose of accelerating hoof growth.

In a further embodiment of the present invention, there is provided a method of treating a hoof crack in a horse, said method comprising administering an effective amount of a compound having somatotropin-like activity or a compound which causes the secretion of somatotropin, as described in the first embodiment of the invention. Cracked hooves are common occurrences in horses and can be debilitating to the animal and costly to the owner. Exogenously administered somatotropin is demonstrated herein to significantly increase the growth rate of horse hooves. As such, the time normally required to regrow a cracked hoof can be significantly reduced.

Somatotropin-based treatment of cracked horse hooves can be used in combination with many of the conventional methods of horse hoof repair in order to further minimize an animal's recovery time from such injuries. Conventional methods suitable for use in combination with somatotropin may include (1) proper balancing of the hoof; (2) corrective shoeing; (3) grooving of the hoof wall; (4) use of clamping across the crack with nails, a Vachette clamp, or mechanical clamps; or (5) use of various prosthetic hoof repair materials such as acrylic, fiberglass, or epoxy resins in combination with umbilical tape or wire, sheet metal screws, or other synthetic materials.

The following example is included to demonstrate one preferred embodiment of the invention. It should be appreciated by those of skill in the art that the techniques disclosed in the examples which follow represent techniques discovered by the inventor to function well in the practice of the invention, and thus can be considered to constitute examples of preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

In order to evaluate the effect of somatotropin on hoof growth, six light horse mares and geldings between 2–22 years of age and weighing between 300–550 kg were given 10 mg/day porcine somatotropin (pST) by daily injection of 10% w/v pST in an excipient containing 65:35 glycerol:water by volume, 0.15% Tween 80 surfactant by volume, pH 6.3 phosphate buffer and 3% potassium chloride by weight. Six additional horses received daily injections of only the excipient. Injections were administered daily for a total of 24 weeks. At the beginning of the study, all horses were given an inverted T brand to the hoof just below the coronary hair line on the dorsal aspect of the hoof. An indelible marker was also used to improve the visibility of the brand. At 4 week intervals, the distance from the hair line to the cross bar of the inverted T brand was determined using a metric ruler. FIG. 1, and the following table, summarize the results obtained over the 24 week period for control and somatotropin-treated groups.

| Hoof Growth (cm) in Response to 10 mg/day Somatotropin | | | | | | | |
|---|---|---|---|---|---|---|---|
| | 0 wk | 4 wk | 8 wk | 12 wk | 16 wk | 20 wk | 24 wk |
| Control | 0 | 0.41 | 0.87 | 1.77 | 2.77 | 3.55 | 4.7 |
| Somatotropin | 0 | 0.57 | 1.18 | 2.1 | 2.93 | 5.27 | 5.7 |

A significant increase in hoof length was observed in the somatotropin-treated group at 8 weeks (p=0.05), 12 weeks (p=0.04), 20 weeks (p<0.0001), and 24 weeks (p<0.0001). Over the entire 24 week treatment period, overall hoof length in the group treated with somatotropin had increased by 26.2% compared to the control group (p<0.0001). These results establish that administration of a mammalian somatotropin can significantly accelerate hoof growth in horses.

---

What is claimed is:

1. A method of accelerating hoof growth in a hoofed animal in need thereof, comprising administering to said animal an effective amount of a compound having somatotropin-like activity or a compound which causes secretion of somatotropin in the animal.

2. The method of claim 1, wherein said compound having somatotropin-like activity is an animal somatotropin.

3. The method of claim 2, wherein the compound is porcine, equine or bovine somatotropin.

4. The method of claim 1, wherein the compound which causes secretion of somatotropin is a growth hormone releasing hormone, a growth hormone releasing peptide, or a growth hormone releasing hormone agonist.

5. The method of claim 1, wherein the hoofed animal is a horse.

6. A method of treating a cracked horse hoof, comprising administering to the horse in an amount effective to accelerate hoof growth a compound having somatotropin-like activity or a compound which causes secretion of somatotropin.

7. The method of claim 6, further comprising the use of a conventional treatment for cracked hooves selected from hoof balancing, corrective shoeing, grooving of the hoof wall, use of clamping across the crack, and prosthetic hoof repair materials.

8. The method of claim 6, wherein said compound having somatotropin-like activity is an animal somatotropin.

9. The method of claim 8, wherein the compound is porcine, equine or bovine somatotropin.

10. The method of claim 6, wherein said compound which causes secretion of somatotropin is a growth hormone releasing hormone, a growth hormone releasing peptide, or a growth hormone releasing hormone agonist.

* * * * *